(12) United States Patent
Scirica

(10) Patent No.: US 7,694,865 B2
(45) Date of Patent: Apr. 13, 2010

(54) SURGICAL STAPLING APPARATUS WITH LOCKING MECHANISM

(75) Inventor: Paul A. Scirica, Huntington, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 0 days.

(21) Appl. No.: 11/657,307

(22) Filed: Jan. 23, 2007

(65) Prior Publication Data

US 2007/0187454 A1 Aug. 16, 2007

Related U.S. Application Data

(63) Continuation of application No. 11/059,773, filed on Feb. 17, 2005, now Pat. No. 7,225,963.

(60) Provisional application No. 60/545,622, filed on Feb. 17, 2004.

(51) Int. Cl.
*A61B 17/68* (2006.01)

(52) U.S. Cl. .............. 227/175.2; 227/175.1; 227/175.4; 227/182.1; 227/19

(58) Field of Classification Search .............. 227/175.1, 227/175.2, 175.4, 182.1, 19
See application file for complete search history.

(56) References Cited

U.S. PATENT DOCUMENTS

| | | | |
|---|---|---|---|
| 3,079,606 | A | 3/1963 | Bobrov et al. |
| 3,490,675 | A | 1/1970 | Green et al. |
| 3,499,591 | A | 3/1970 | Green |
| 4,244,372 | A | 1/1981 | Kapitanov et al. |
| 4,429,695 | A | 2/1984 | Green |
| 4,520,817 | A | 6/1985 | Green |
| 4,589,413 | A | 5/1986 | Malyshev et al. |
| 4,605,001 | A | 8/1986 | Rothfuss et al. |
| 4,608,981 | A | 9/1986 | Rothfuss et al. |
| 4,610,383 | A | 9/1986 | Rothfuss et al. |
| 4,633,861 | A | 1/1987 | Chow et al. |
| 4,633,874 | A | 1/1987 | Chow et al. |
| 4,672,964 | A | 6/1987 | Dee et al. |

(Continued)

FOREIGN PATENT DOCUMENTS

DE 4300307 7/1994

(Continued)

OTHER PUBLICATIONS

European Search Report for EP 07007782.1 date of completion is Jun. 15, 2007 (8 pages).

*Primary Examiner*—Rinaldi I. Rada
*Assistant Examiner*—Michelle Lopez

(57) ABSTRACT

The present disclosure provides for a loading unit for use with and/or supportable on a distal end of a surgical stapling apparatus. The loading unit includes a housing portion including a distal end and a proximal end, a drive assembly slidably supported within the housing portion of the loading unit, and a locking mechanism pivotally supported on the housing portion of the loading unit, the locking mechanism having a first position wherein the locking mechanism engages a portion of the drive assembly and maintains the position, preferably the axial position, of the drive assembly relative to the housing portion of the loading unit, and the locking mechanism having a second position wherein the locking mechanism disengages the drive assembly and enables the drive assembly to move relative to the housing portion.

18 Claims, 17 Drawing Sheets

U.S. PATENT DOCUMENTS

| | | |
|---|---|---|
| 4,763,669 A | 8/1988 | Jaeger |
| 4,863,088 A | 9/1989 | Redmond et al. |
| 4,880,015 A | 11/1989 | Nieman |
| 4,892,244 A | 1/1990 | Fox et al. |
| 4,978,049 A | 12/1990 | Green |
| 4,991,764 A | 2/1991 | Mericle |
| 5,040,715 A | 8/1991 | Green et al. |
| 5,065,929 A | 11/1991 | Schulze et al. |
| 5,071,052 A | 12/1991 | Rodak et al. |
| 5,074,454 A | 12/1991 | Peters |
| 5,083,695 A | 1/1992 | Foslien et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,152,279 A | 10/1992 | Wilk |
| 5,209,747 A | 5/1993 | Knoepfler |
| RE34,519 E | 1/1994 | Fox et al. |
| 5,275,608 A | 1/1994 | Forman et al. |
| 5,282,826 A | 2/1994 | Quadri |
| 5,307,976 A | 5/1994 | Olson et al. |
| 5,312,023 A | 5/1994 | Green et al. |
| 5,318,221 A | 6/1994 | Green et al. |
| 5,326,013 A | 7/1994 | Green et al. |
| 5,330,502 A | 7/1994 | Hassler et al. |
| 5,332,142 A | 7/1994 | Robinson et al. |
| 5,350,391 A | 9/1994 | Iacovelli |
| 5,354,311 A | 10/1994 | Kambin et al. |
| 5,374,277 A | 12/1994 | Hassler |
| 5,376,095 A | 12/1994 | Ortiz |
| 5,383,888 A | 1/1995 | Zvenyatsky et al. |
| 5,397,046 A | 3/1995 | Savage et al. |
| 5,415,334 A | 5/1995 | Williamson, IV et al. |
| 5,415,335 A | 5/1995 | Knodel, Jr. |
| 5,433,721 A | 7/1995 | Hooven et al. |
| 5,465,895 A | 11/1995 | Knodel et al. |
| 5,467,911 A | 11/1995 | Tsuruta et al. |
| 5,474,566 A | 12/1995 | Alesi et al. |
| 5,474,571 A | 12/1995 | Lang |
| 5,484,451 A | 1/1996 | Akopov et al. |
| 5,486,185 A | 1/1996 | Freitas et al. |
| 5,487,500 A | 1/1996 | Knodel et al. |
| 5,507,426 A | 4/1996 | Young et al. |
| 5,535,935 A | 7/1996 | Vidal et al. |
| 5,582,617 A | 12/1996 | Kliman et al. |
| 5,584,425 A | 12/1996 | Savage et al. |
| 5,605,272 A | 2/1997 | Witt et al. |
| 5,630,539 A | 5/1997 | Plyley et al. |
| 5,634,584 A | 6/1997 | Okorocha et al. |
| 5,762,255 A | 6/1998 | Chrisman et al. |
| 5,797,537 A | 8/1998 | Oberlin et al. |
| 5,820,009 A | 10/1998 | Melling et al. |
| 5,893,506 A | 4/1999 | Powell |
| 5,901,895 A | 5/1999 | Heaton et al. |
| 6,010,054 A | 1/2000 | Johnson et al. |
| 6,032,849 A | 3/2000 | Mastri et al. |
| 6,079,606 A | 6/2000 | Milliman et al. |
| 6,109,500 A | 8/2000 | Alli et al. |
| 6,241,139 B1 | 6/2001 | Milliman et al. |
| 2005/0184124 A1 | 8/2005 | Scirica et al. |

FOREIGN PATENT DOCUMENTS

| | | |
|---|---|---|
| EP | 0484677 | 5/1992 |
| EP | 0589306 | 3/1994 |
| EP | 0591946 | 4/1994 |
| EP | 0592243 | 4/1994 |
| EP | 0621009 | 10/1994 |
| EP | 0656188 | 6/1995 |
| FR | 2681775 | 10/1991 |

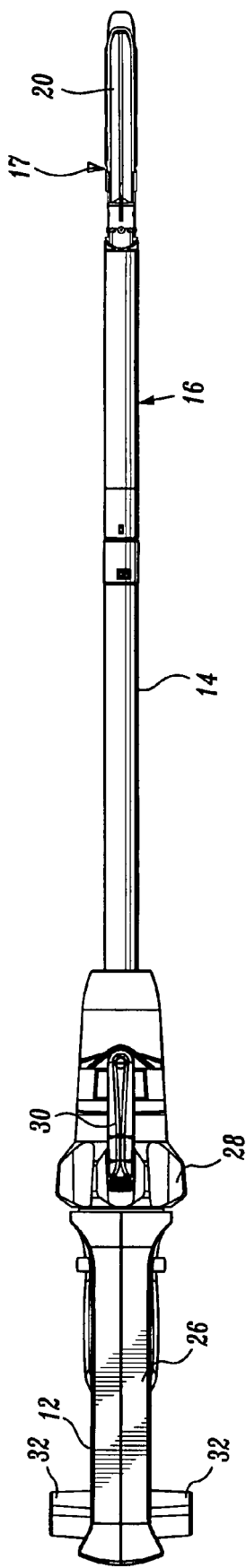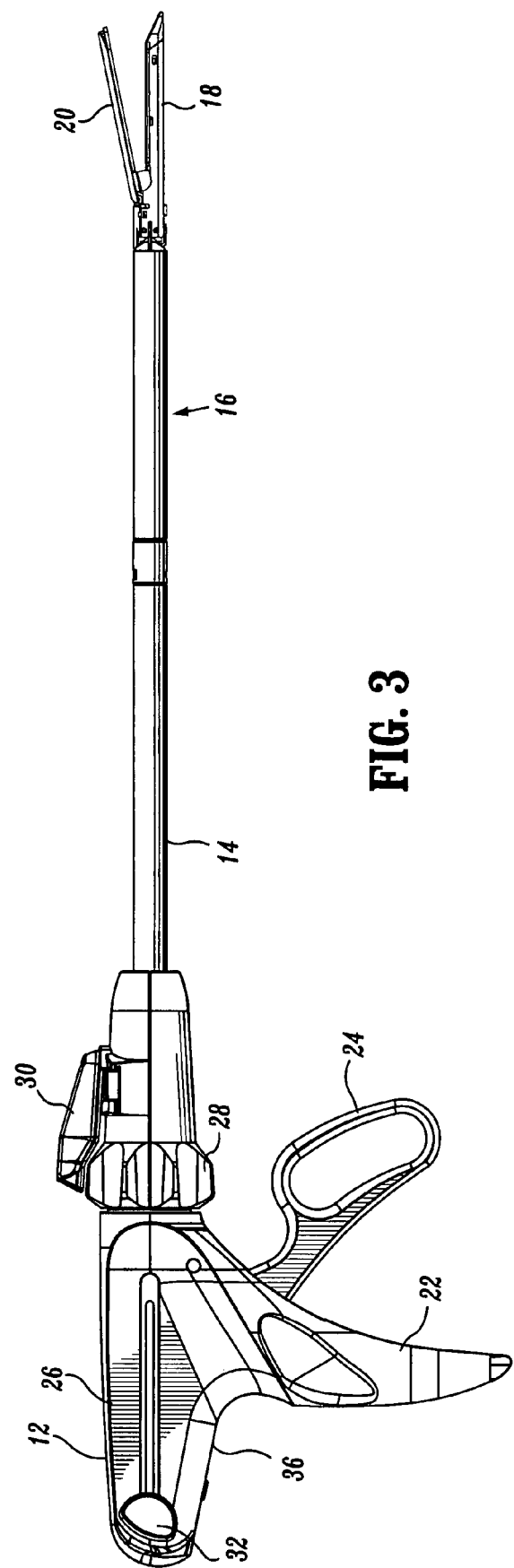
FIG. 2
FIG. 3

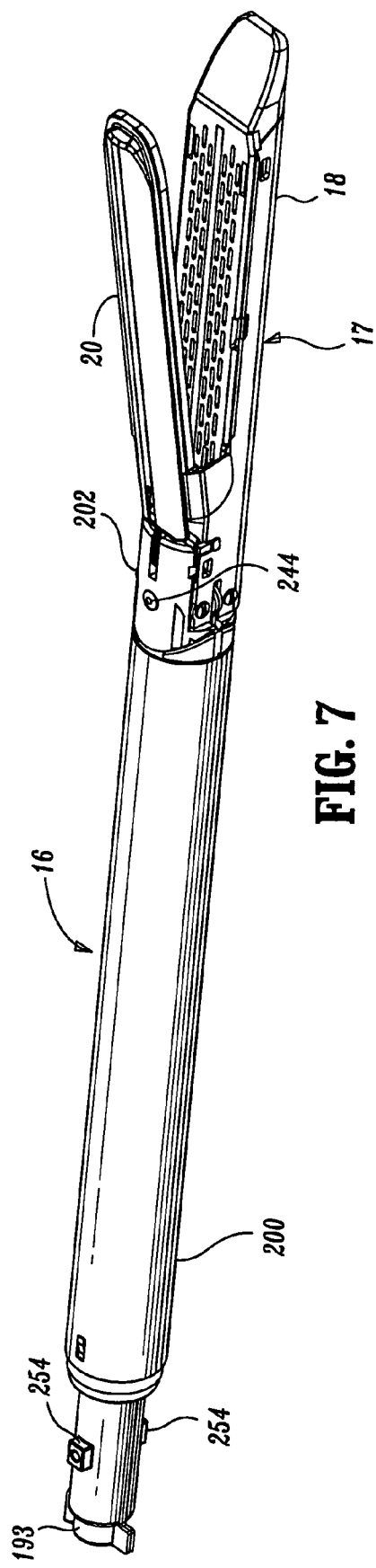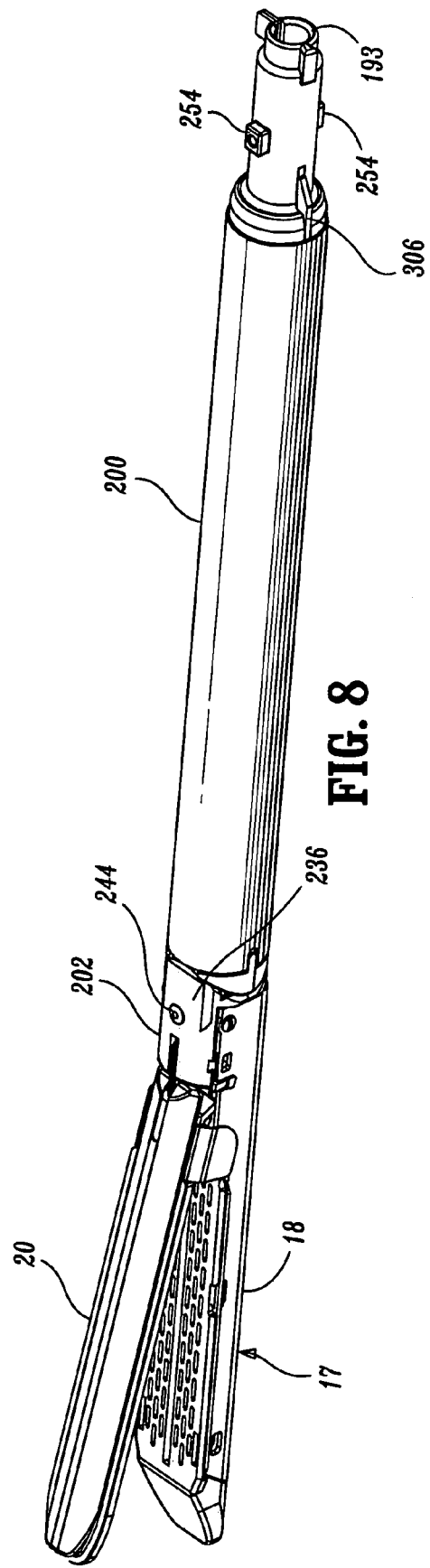

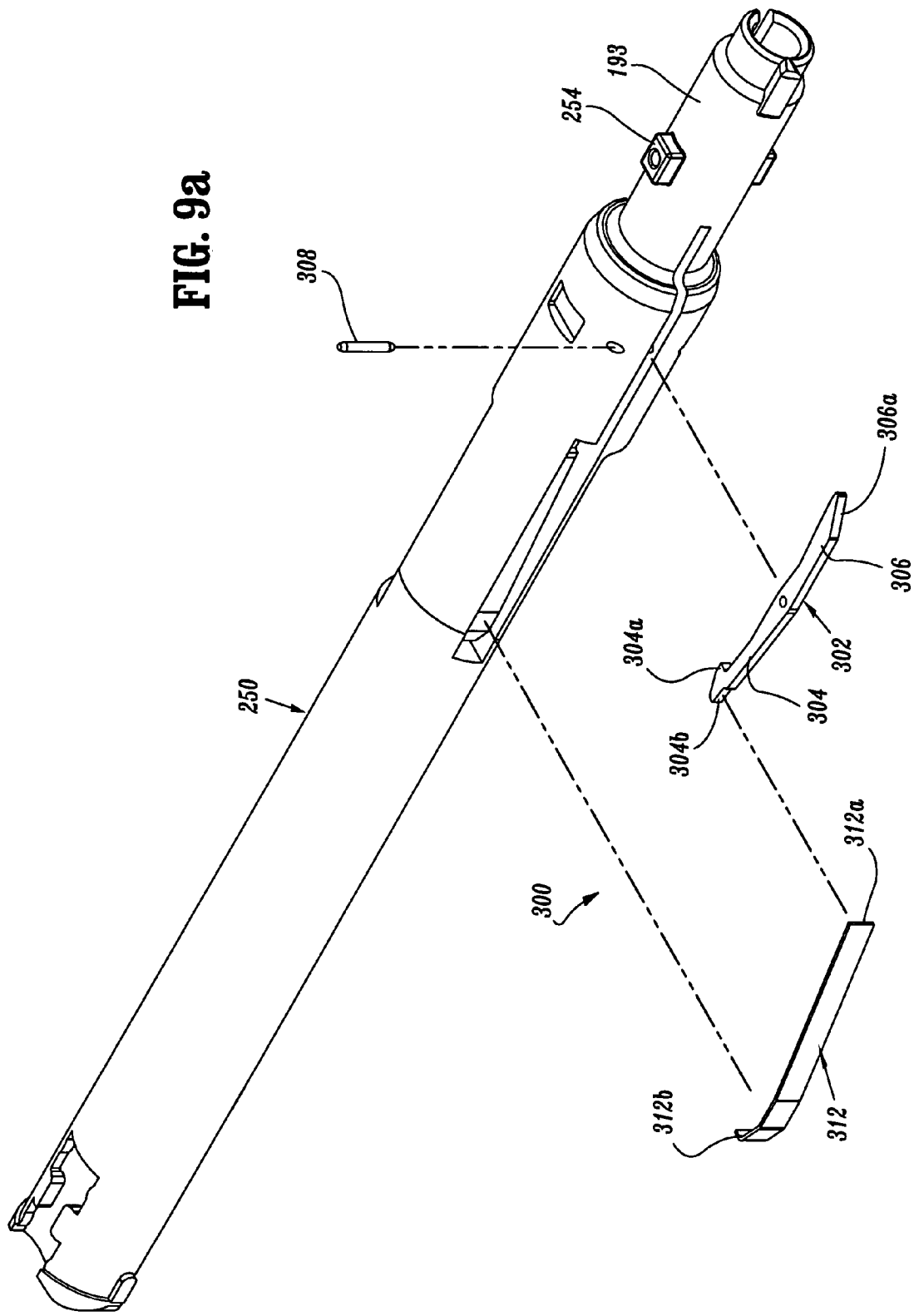

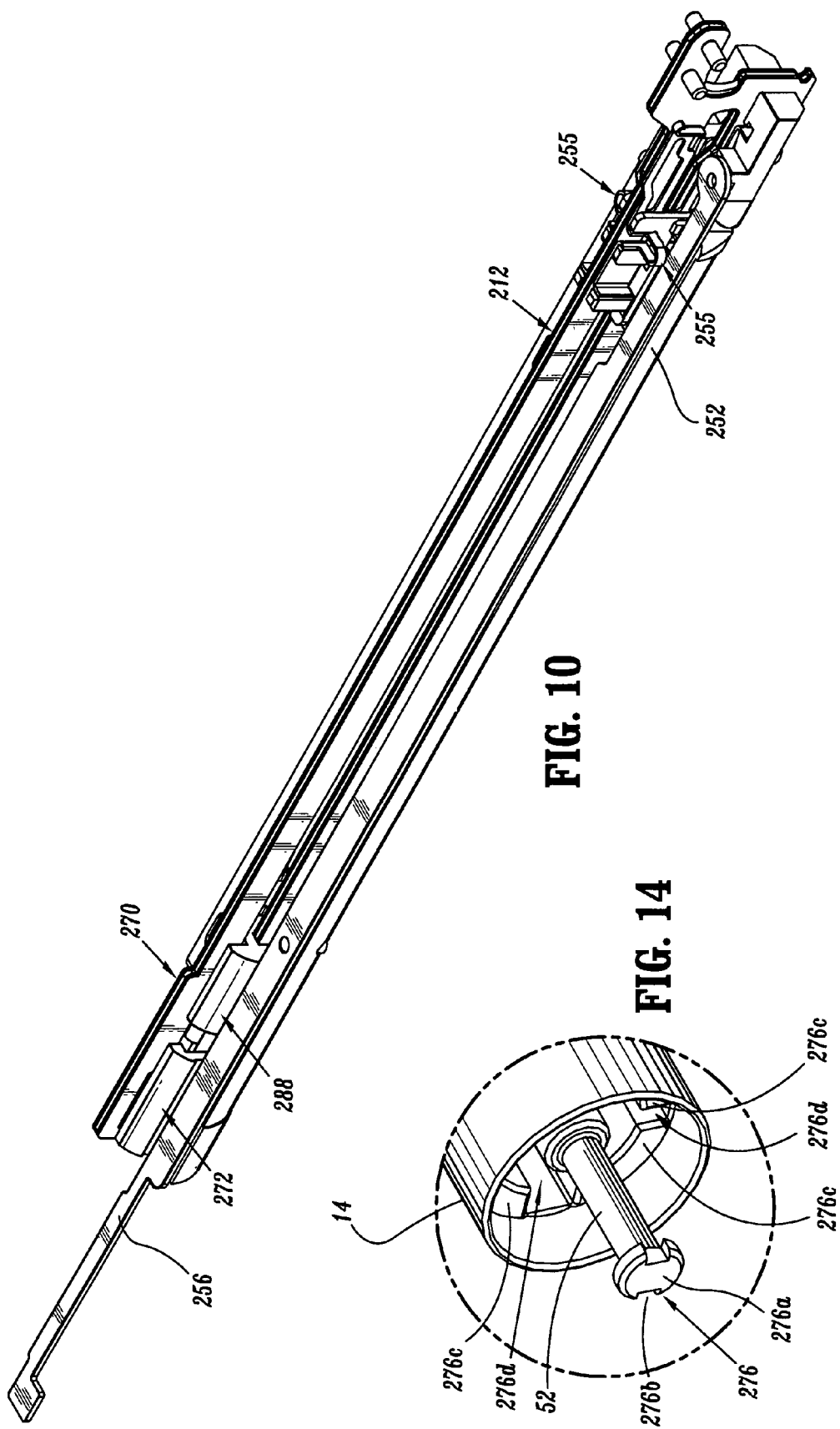

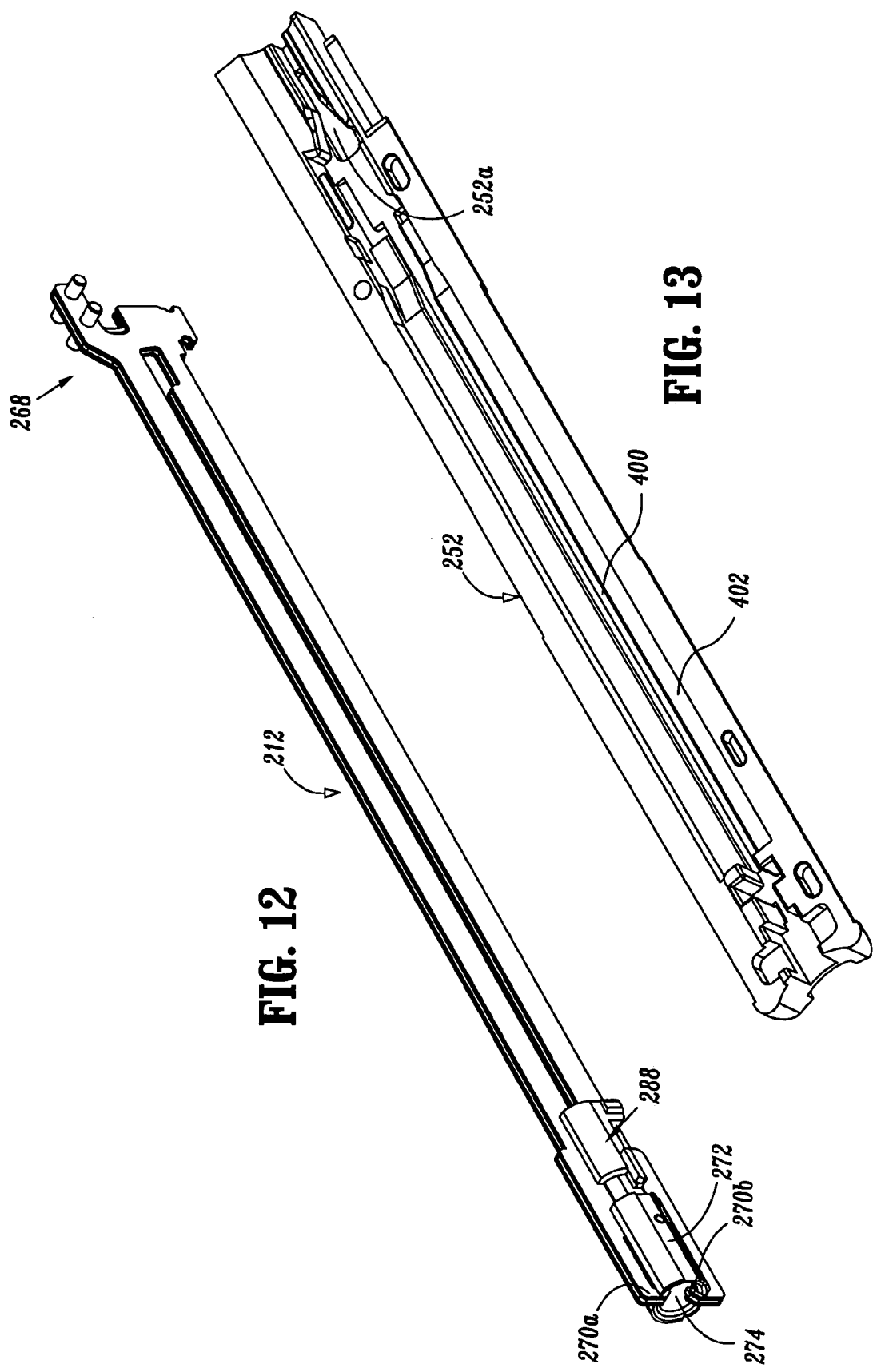

SURGICAL STAPLING APPARATUS WITH LOCKING MECHANISM

CROSS-REFERENCE TO RELATED APPLICATION

This application is a continuation of U.S. patent application Ser. No. 11/059,773 filed on Feb. 17, 2005, now U.S. Pat. No. 7,225,963, which claims the benefit of and priority to U.S. Provisional Application Ser. No. 60/545,622, filed Feb. 17, 2004, the entire content of which being incorporated herein by reference.

BACKGROUND

1. Technical Field

The present disclosure relates to a surgical apparatus, e.g., a surgical stapling apparatus. More particularly, the present disclosure relates to an endoscopic surgical stapling apparatus that includes a locking mechanism that includes a locking member for retaining the drive assembly of a loading unit, e.g., a single use loading unit ("SULU") or disposable loading unit ("DLU"), at a substantially fixed axial position until the SULU or DLU has been loaded with or secured to a surgical stapling apparatus, to ensure proper or complete engagement of the SULU or DLU, especially its drive assembly, to the surgical stapling apparatus. For simplicity, hereinafter, SULU or DLU will be referred to as "DLU", but it should be understood to include either or both a DLU or SULU.

2. Background of Related Art

Surgical devices wherein tissue is first grasped or clamped between opposing jaw structure and then joined by surgical fasteners are well known in the art. In some instruments a knife is provided to cut the tissue which has been joined by the fasteners. The fasteners are typically in the form of surgical staples but two part polymeric fasteners can also be utilized.

Instruments for this purpose can include two elongated jaw members which are respectively used to capture or clamp tissue. Typically, one of the jaw members carries a staple cartridge which houses a plurality of staples arranged in at least two lateral rows while the other jaw member has an anvil that defines a surface for forming the staple legs as the staples are driven from the staple cartridge. Generally, the stapling operation is effected by cam members that travel longitudinally through the staple cartridge, with the cam members acting upon staple pushers to sequentially eject the staples from the staple cartridge. A knife can travel between the staple rows to longitudinally cut and/or open the stapled tissue between the rows of staples. Such instruments are disclosed, for example, in U.S. Pat. No. 3,079,606 and U.S. Pat. No. 3,490,675.

A later stapler disclosed in U.S. Pat. No. 3,499,591 also applies a double row of staples on each side of the incision. This patent discloses a surgical stapler that has a disposable loading unit in which a cam member moves through an elongate guide path between two sets of staggered staple carrying grooves. Staple drive members are located within the grooves and are positioned in such a manner so as to be contacted by the longitudinally moving cam member to effect ejection of the staples from the staple cartridge of the disposable loading unit. Other examples of such staplers are disclosed in U.S. Pat. Nos. 4,429,695 and 5,065,929.

Each of the instruments described above is designed for use in conventional surgical procedures wherein surgeons have direct manual access to the operative site. However, in endoscopic or laparoscopic procedures, surgery is performed through a small incision or through a narrow cannula inserted through small entrance wounds in the skin. In order to address the specific needs of endoscopic and/or laparoscopic surgical procedures, endoscopic surgical stapling devices have been developed and are disclosed in, for example, U.S. Pat. No. 5,040,715 (Green, et al.); U.S. Pat. No. 5,307,976 (Olson, et al.); U.S. Pat. No. 5,312,023 (Green, et al.); U.S. Pat. No. 5,318,221 (Green, et al.); U.S. Pat. No. 5,326,013 (Green, et al.); U.S. Pat. No. 5,332,142 (Robinson, et al.); and U.S. Pat. No. 6,241,139 (Milliman et al.), the entire contents of each of which are incorporated herein by reference.

Tyco Healthcare Group, LP, the assignee of the present application, has manufactured and marketed endoscopic stapling instruments, such as the Multifire ENDO GIA™ 30 and Multifire ENDO GIA™ 60 instruments, for a number of years. These instruments include a surgical stapling apparatus and a DLU. Typically, the DLU is attached to the apparatus immediately prior to surgery. After use, the DLU can be removed from the apparatus and a new DLU can be fastened to the apparatus to perform additional stapling and/or cutting operations. These instruments have provided significant clinical benefits. Nonetheless, improvements to these instruments are still possible.

It would be desirable to provide an improved DLU for a surgical stapling apparatus and an improved surgical stapling apparatus having the DLU loaded thereon.

It would also be desirable to provide a locking mechanism for a DLU to assure proper loading of the DLU to the shaft of a surgical stapling apparatus.

Accordingly, it is an object of this disclosure to provide an improved DLU which locks or retains its drive assembly in proper position to be loaded onto the shaft of a surgical stapling apparatus (hereinafter referred to as the or a "ready-to-load position") until the DLU is loaded onto a surgical stapling apparatus to assure that when the DLU is loaded thereto, the drive assembly is properly engaged by, coupled to or connected to a drive member of the shaft, thereby helping to ensure proper operation of the DLU and the surgical stapling apparatus. For example, with the DLU loaded onto the surgical stapling apparatus, after firing of the surgical stapling apparatus, retraction of the control rod will unapproximate or open and/or unclamp the anvil and cartridge assemblies.

An object of the disclosure is to provide an improved DLU that includes a locking mechanism that retains the drive assembly in such a ready-to-load position until the DLU is loaded onto the surgical stapling apparatus.

Another object of the present disclosure is to provide a locking mechanism for a DLU and a DLU having a locking mechanism, such that firing of the surgical stapling apparatus is prevented unless and until the DLU is loaded onto the shaft of the surgical stapling apparatus.

Yet another object of the disclosure is to provide a DLU that, after firing, can be disconnected from the surgical stapling apparatus.

Yet another object of the disclosure is to provide a DLU that has only two conditions, one in which it is not loaded and its drive assembly is locked or retained in the ready-to-load position, and another in which the DLU is loaded onto the shaft of a surgical stapling apparatus and in which the drive assembly is unlocked and free to be actuated.

Still another object of the present disclosure is to provide the above objects in a roticulating, i.e., roticulable, DLU.

SUMMARY

In accordance with the present disclosure, a surgical apparatus, e.g., a surgical stapling apparatus, including a locking mechanism for ensuring proper engagement of a disposable loading unit to an end, preferably the distal end, of the surgical apparatus is provided. According to one aspect of the present disclosure, the surgical apparatus includes a housing, a handle supported by the housing, and a loading unit supportable on a distal end of the housing. The loading unit includes a housing portion including a distal end and a proximal end, a drive assembly slidably supported within the housing portion of the loading unit, and a locking mechanism pivotally supported on the housing portion of the loading unit. The locking mechanism can have a first position wherein the locking mechanism engages a portion of the drive assembly and maintains the position of the drive assembly relative to the housing portion of the loading unit. The locking mechanism can have a second position wherein the locking mechanism disengages the drive assembly and enables the drive assembly to move relative to the housing portion.

It is envisioned that the locking mechanism can include a lever pivotably connected to the housing portion ad defining a pivot point. The lever includes a distal end extending distally of the pivot point and a proximal end extending proximally of the pivot point. The distal end of the lever preferably includes a member, preferably a hook, for selectively engaging the portion of the drive assembly, wherein when the locking mechanism is in the first position the hook engages a portion of the drive assembly and when the locking mechanism is in the second position the hook is disengaged from the portion of the drive assembly.

It is envisioned that when the locking mechanism is moved from the first position, to the second position the proximal end of the lever is moved radially inward and the distal end of the lever is moved radially outward. The locking mechanism is moved from the first position to the second position upon the coupling of the loading unit to the distal end of the elongate body. Preferably, the locking mechanism is moved from the first position to the second position by a twisting action of the loading unit relative to the elongate body when the insertion tip of the loading unit is inserted in to the distal end of the elongate body.

The locking mechanism can further include a biasing member operatively associated therewith. Preferably, the biasing member biases the lever to the first-position.

It is envisioned that when the locking mechanism is in the first position, the proximal-end of the lever extends radially beyond an outer surface of the housing portion. Desirably, the proximal end of the lever of the locking mechanism may define an angled surface to facilitate connection with the elongate body.

Preferably, the surgical apparatus is a fastener applier or stapler, preferably a laparoscopic or endoscopic stapler.

This disclosure also is of a DLU, preferably a roticulator DLU for a surgical fastener applier or stapler.

Desirably, the proximal end of the housing portion of the loading unit defines an insertion tip.

It is envisioned that the surgical apparatus may include an elongate body extending distally from the housing.

The present disclosure further provides for a loading unit for use with and/or supportable on a distal end of a surgical stapling apparatus. The loading unit includes a housing portion including a distal end and a proximal end, a drive assembly slidably supported within the housing portion of the loading unit, and a locking mechanism supported on the housing portion of the loading unit, the locking mechanism having a first position wherein the locking mechanism engages a portion of the drive assembly and maintains the position, preferably the axial position, of the drive assembly relative to the housing portion of the loading unit, and the locking mechanism having a second position wherein the locking mechanism disengages the drive assembly and enables the drive assembly to move relative to the housing portion.

Additional advantages will become apparent from the description which follows, taken in conjunction with the accompanying drawings.

BRIEF DESCRIPTION OF THE DRAWINGS

The present disclosure will be further described with reference to the accompanying drawings, wherein like reference numerals refer to like parts in the several views, and wherein:

FIG. 2 is a top view of the surgical stapling apparatus shown in FIG. 1;

FIG. 3 is a side view of the surgical stapling apparatus shown in FIGS. 1 and 2;

FIG. 7 is a top perspective view of the DLU of FIG. 6;

FIG. 8 is a top perspective view of the DLU of FIGS. 6 and 7;

FIG. 9a is an enlarged top perspective view of the proximal portion of the upper housing half of the DLU of FIGS. 6-9;

FIG. 10 is a top perspective view of the proximal housing portion and mounting assembly of the DLU of FIGS. 6-9 with the upper housing half removed;

FIG. 12 is a top perspective view of the axial drive assembly of FIG. 11 of the DLU of FIGS. 6-9;

FIG. 13 is an enlarged top perspective view of a lower housing half of the proximal housing portion of the DLU of FIGS. 6-9;

FIG. 14 is an enlarged perspective view of the distal end of the elongated body of the stapling apparatus shown in FIG. 4;

DETAILED DESCRIPTION OF PREFERRED EMBODIMENTS

Figure 1:
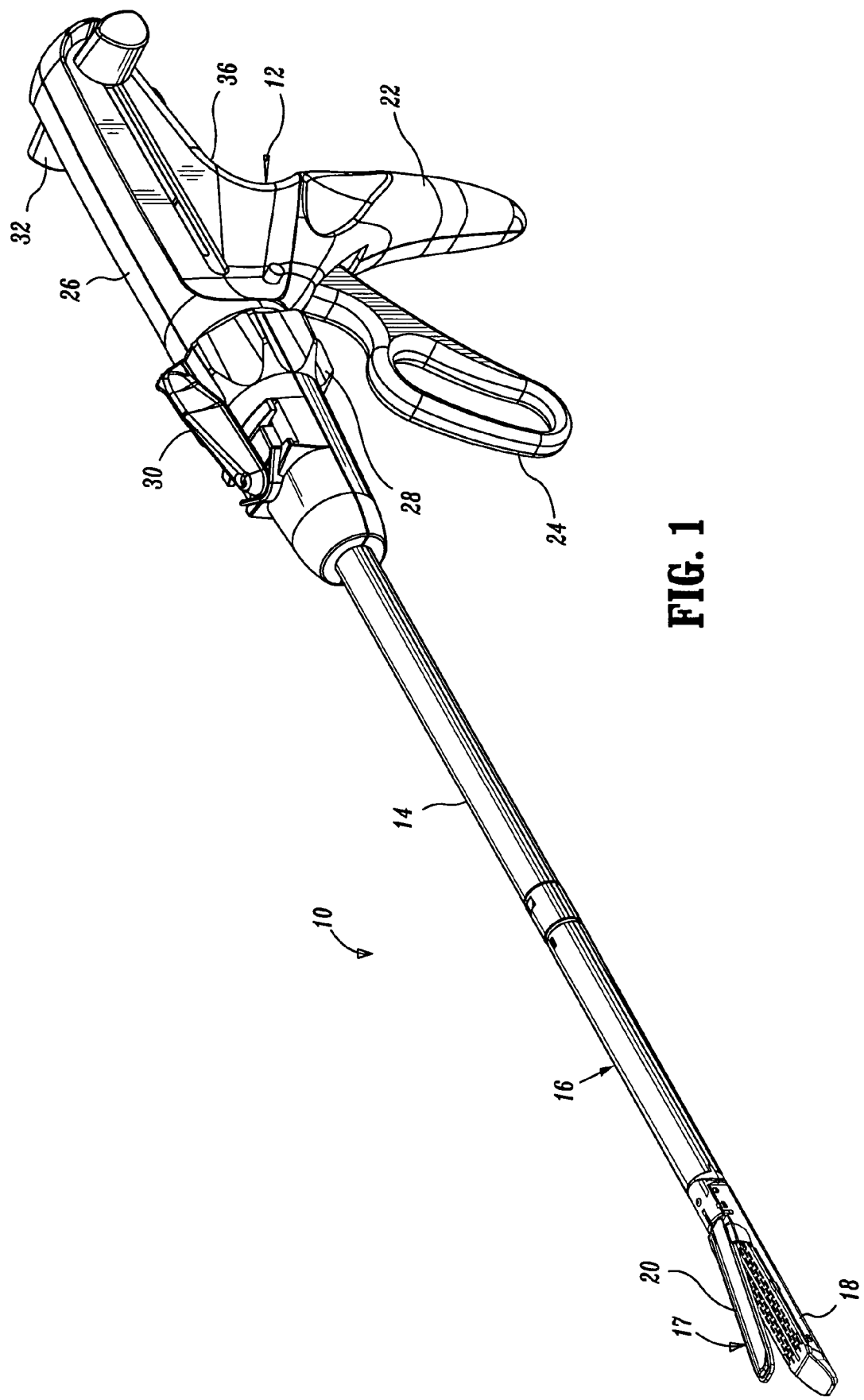
FIG. 1 is a top perspective view of a preferred embodiment of the presently disclosed surgical stapling apparatus.

Preferred embodiments of the presently disclosed surgical apparatus, DLU and locking mechanism or member will now be described in detail with reference to the drawings, in which like reference numerals designate identical or corresponding elements in each of the several views.

In the drawings and in the description that follows, the term "proximal", as is traditional, will refer to the end of the stapling apparatus which is closest to the operator, while the term "distal" will refer to the end of the apparatus which is furthest from the operator.

FIGS. 1-4 show a surgical apparatus, e.g., surgical stapling apparatus, generally referred to as 10. In the interest of brevity, this disclosure will focus primarily on systems, methods and structures for loading, engaging, coupling or connecting a disposable loading unit ("DLU") 16 to surgical stapling apparatus 10. A detailed discussion of the remaining components and method of use of surgical stapling apparatus 10, is disclosed in U.S. Pat. No. 6,241,139.

Surgical stapling apparatus 10 is an endoscopic apparatus and includes a handle assembly 12 and an elongated body 14 extending from handle assembly 12. A DLU 16 is releasably secured to the distal end of elongated body 14. While this disclosure relates to the use of a DLU with surgical stapling apparatus 10, it is understood and within the scope of the present disclosure that a single use loading unit (SULU) or other end effector and/or tool assembly can equally be used in cooperation with surgical stapling apparatus 10.

DLU 16 includes a tool 17 having a cartridge assembly 18 housing a plurality of surgical staples (not shown) and an anvil assembly 20 movably secured in relation to cartridge assembly 18. As shown herein, DLU 16 is configured to apply six (6) linear rows of staples, in DLU's measuring from about 30 mm to about 60 mm in length. DLUs for applying any number of rows of staples, having staple pockets arranged in various patterns and/or DLUs and end effectors having any other lengths, e.g., 45 mm, are also envisioned. Handle assembly 12 includes a stationary handle member 22, a movable handle member 24, and a barrel portion 26.

A rotatable member 28 preferably is mounted on the forward end of barrel portion 26 to facilitate rotation of elongated body 14 and attached DLU 16 with respect to handle assembly 12. An articulation lever 30 preferably is also mounted on the forward end of barrel portion 26 adjacent rotatable member 28 to facilitate articulation of tool assembly 17. Preferably, a pair of knobs 32 are movably positioned along barrel portion 26. Knobs 32 are advanced distally to approximate or close cartridge and/or anvil assembly 18, 20, and retracted proximally to unapproximate or open cartridge and/or anvil assembly 18, 20.

Figure 4:
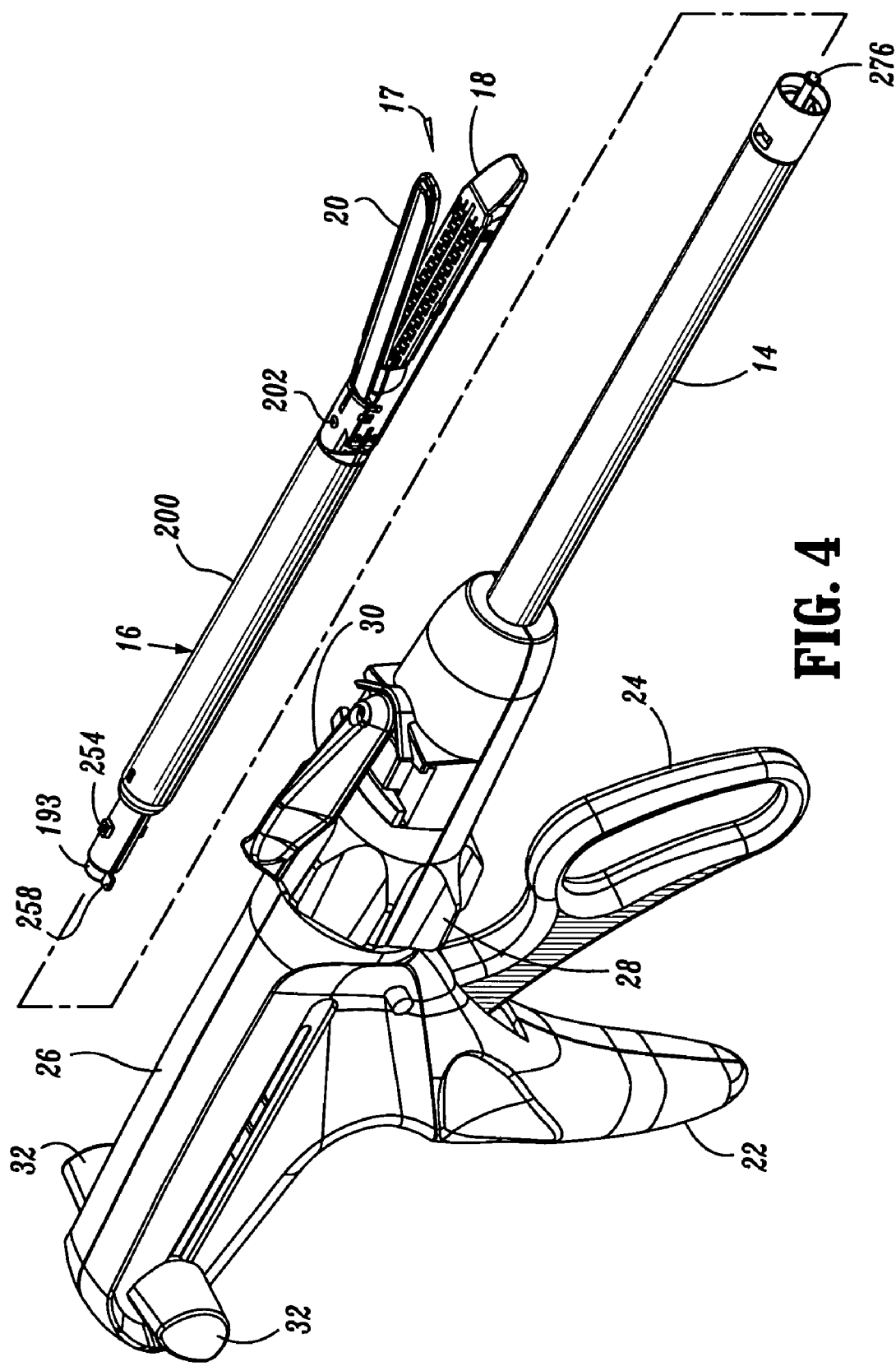
FIG. 4 is a top perspective view of the surgical stapling apparatus of FIGS. 1-3 with the DLU disengaged from the elongate body of the surgical stapling apparatus.

As seen in FIG. 4, DLU 16 is desirably selectively removably couplable to elongated body 14. DLU 16 includes a housing portion 200 having a proximal end adapted to releasably engage the distal end of elongated body 14. A mounting assembly 202 is pivotally secured at 203 to the distal end of housing portion 200, and is configured to receive the proximal end of tool assembly 17 such that pivotal movement of mounting assembly 202 about an axis at 203 perpendicular to the longitudinal axis of housing portion 200 effects articulation of tool assembly 17.

Figure 5:
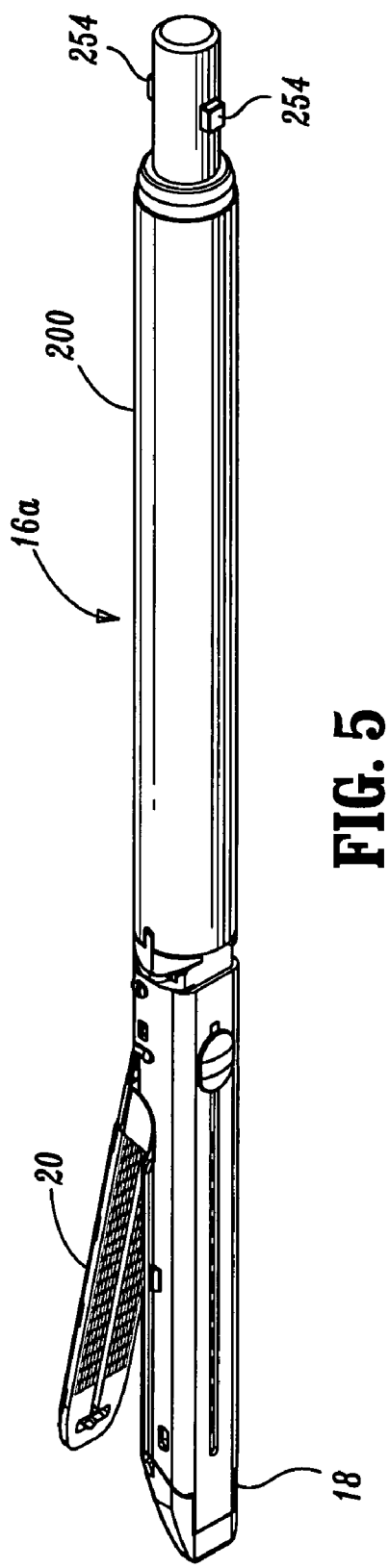
FIG. 5 is a bottom perspective view of a non-articulating DLU for use with the surgical stapling apparatus of FIGS. 1-4.
Figure 6:
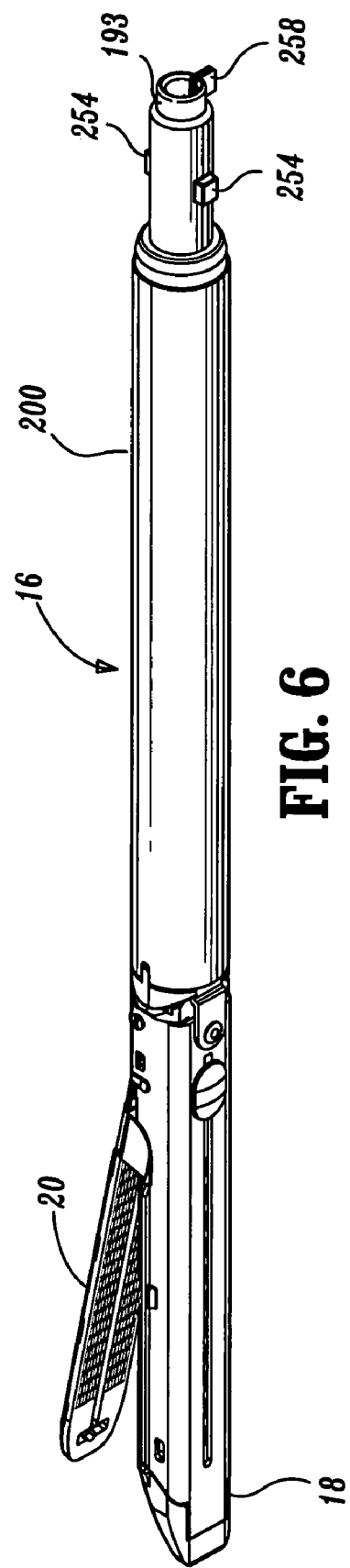
FIG. 6 is a bottom perspective view of the preferred articulating DLU of the surgical stapling apparatus of FIGS. 1-4.

Surgical stapling apparatus 10 is capable of receiving a non-articulating DLU 16a, as seen in FIG. 5, or an articulating DLU 16, as seen in FIGS. 6-8. U.S. Pat. No. 6,241,139 includes a detailed discussion of articulating and non-articulating DLU.

With general reference to FIGS. 9, 9a, 10-13, 15 and 17-23 and particular reference to FIGS. 9, 9a, 15, 17 and 18, DLU 16 includes a mounting assembly 235. Mounting assembly 235 includes an upper and a lower mounting portion 236, 238, respectively. A centrally located pivot member 284 extends from each of upper and lower mounting portions 236, 238 through respective openings 246a formed in coupling members 246. Coupling members 246 each include an interlocking proximal portion 246b configured to be received in grooves 290 formed in the proximal end of upper and lower housing halves 250, 252 to retain mounting assembly 235 and upper and lower housing halves 250, 252 in a longitudinally fixed position in relation to each other.

Upper housing half 250 and lower housing half 252 are contained within an outer sleeve, shell or casing 251. The proximal end of upper housing half 250 includes radially outwardly extending engagement nubs 254 for releasably engaging the distal end of body 14. Nubs 254 form a bayonet-type coupling with the distal end of body 14. Housing halves 250 and 252 define a channel 400 for slidably receiving axial drive assembly 212 therein. An articulation link 256 is dimensioned to be slidably positioned within a slot 402 formed in upper and lower housing halves 250, 252. A pair of blow out plate assemblies 255 are positioned adjacent the distal end of housing portion 200 adjacent the distal end of axial drive assembly 212 to prevent outward buckling and bulging of drive assembly 212 during articulation and firing of surgical stapling apparatus 10. For a detailed discussion of the structure and operation of blow out plate assemblies 255, reference is made to International Application Serial No. PCT/US02/32031, filed on Oct. 4, 2002, entitled "Surgical Stapling Device", the entire content of which is herein incorporated by reference.

Figure 9:
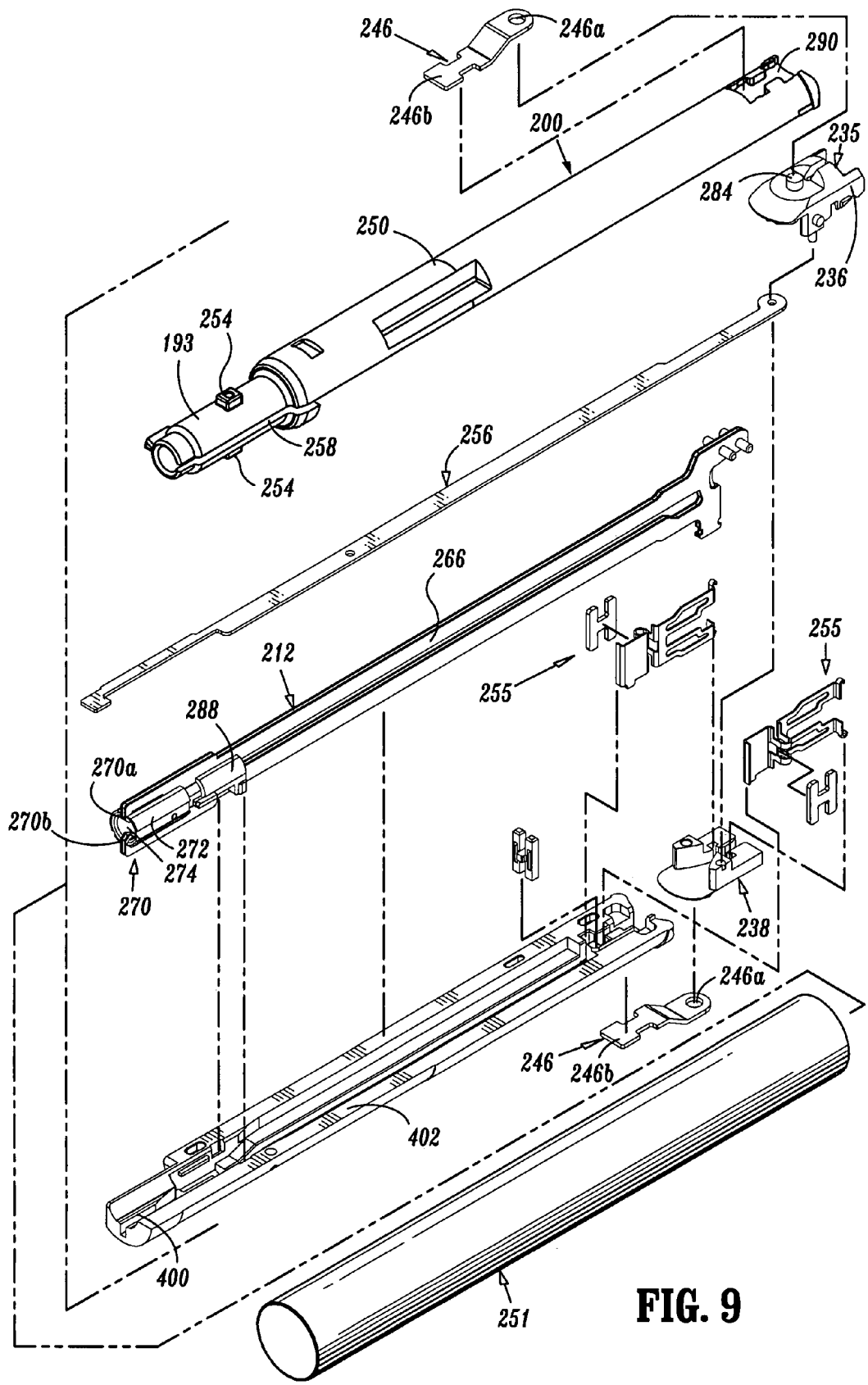
FIG. 9 is an enlarged top perspective view, with parts separated, of the proximal housing portion and mounting assembly of the DLU of FIGS. 6-8.

Referring to FIG. 9, optionally, a locking member 288 may be supported on engagement section 270 of axial drive assembly 212. In operation, when axial drive assembly 212 is actuated, by applying a predetermined force to movable handle member 24 to advance axial drive assembly 212 distally, locking member 288 provides an audible and tactile indication that surgical stapling apparatus 10 has been actuated. For a detailed discussion of the structure and operation of locking member 288, reference is made to the aforementioned International Application Serial No. PCT/US02/32031. Locking member 288 may also prevent inadvertent partial actuation of DLU 16, such as during shipping, by locking axial drive assembly 212 at a fixed position within DLU 16 until a predetermined axial force has been applied to axial drive assembly 212.

Figure 11:
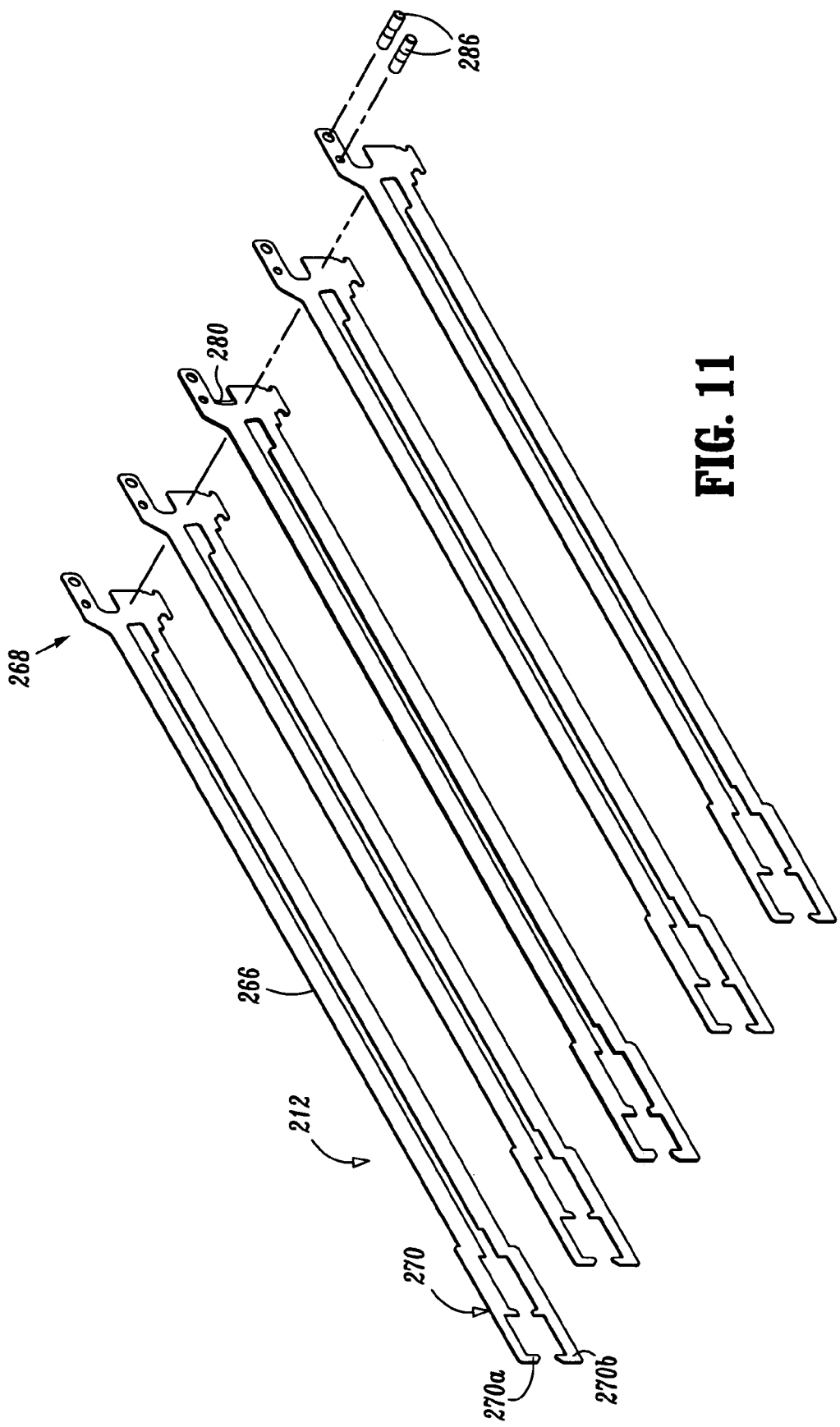
FIG. 11 is a top perspective view, with parts separated, of the axial drive assembly of the DLU of FIGS. 6-9.

With reference to FIGS. 9-12, axial drive assembly 212 includes an elongated drive beam 266 (FIG. 11) including a distal working head 268 (FIG. 12) and a proximal engagement section 270. Drive beam 266 may be constructed from a single sheet of material or, preferably, multiple stacked sheets, as shown in FIG. 11. Engagement section 270 includes a pair of resilient engagement fingers 270a and 270b which are dimensioned and configured to mountingly engage a pair of corresponding retention slots 272a and 272b formed in drive member 272 (FIG. 12). Drive member 272 includes a proximal porthole 274 configured to receive distal end 276 of a drive member, e.g., drive rod or control rod 52 (FIGS. 14 and 16-18) when the proximal end of DLU 16 is being engaged with elongated body 14 of surgical stapling apparatus 10. Control rod 52 functions to impart axial movement of drive assembly 212 from handle assembly 12.

With reference to FIGS. 9, 9a and 15-32, DLU 16 further includes a locking mechanism 300, preferably pivotably supported on a housing, e.g., on upper housing half 250. Locking mechanism 300 is manipulatable from a first position, in which drive assembly 212 is maintained in a ready-to-load position for proper loading, to a second position, in which drive assembly 212 is free to move. DLU 16 is considered to be loaded to elongate body 14 when locking mechanism 300 is in the second position, i.e., when drive assembly 212 is connected to control rod 52 of elongate body 14. As seen in FIGS. 9, 9a and 15-23, locking mechanism 300 includes a lever 302 pivotally connected to upper housing half 250 by a pivot pin 308 extending therethrough, thereby defining a pivot point. Lever 302 includes a free distal end 304 extending distally of pivot pin 308 and a free proximal end 306 extending proximally of pivot pin 308. Proximal end 306 of lever 302 terminates in an angled surface 306a formed along an upper surface thereof for engaging a portion of elongate body 14, as will be discussed in greater detail below. Distal end 304 of lever 302 terminates in a hook member 304a formed along a lower surface thereof for engaging drive member 272, as will be discussed in greater detail below.

Locking mechanism 300 further includes a biasing member or spring 312, preferably a leaf spring, operatively associated with upper housing half 250 and distal end 304 of lever 302. Preferably, spring 312 maintains lever 302 in the first position such that hook member 304a is engaged with drive member 272. Spring 312 includes a proximal end 312a operatively associated with distal end 304 of lever 302, and a distal end 312b secured to upper housing half 250. Preferably, distal end 312b is in the form of a hook or bent arm extending into a slot or groove 250a (see FIGS. 17-20) in upper housing half 250 in such a manner so as to create a force "F" acting radially inward at proximal end 312a of spring 312 (see FIG. 17). Proximal end 312a is positioned in engagement with an outer surface 304b of distal end 304 of lever 302. As such, force "F" in turn acts on distal end 304 of lever 302 to thereby urge distal end 304 radially inward as well. In so doing, proximal end 306 of lever 302 is urged radially outward due to the pivoting action of lever 302 about pivot pin 308.

Figure 15:
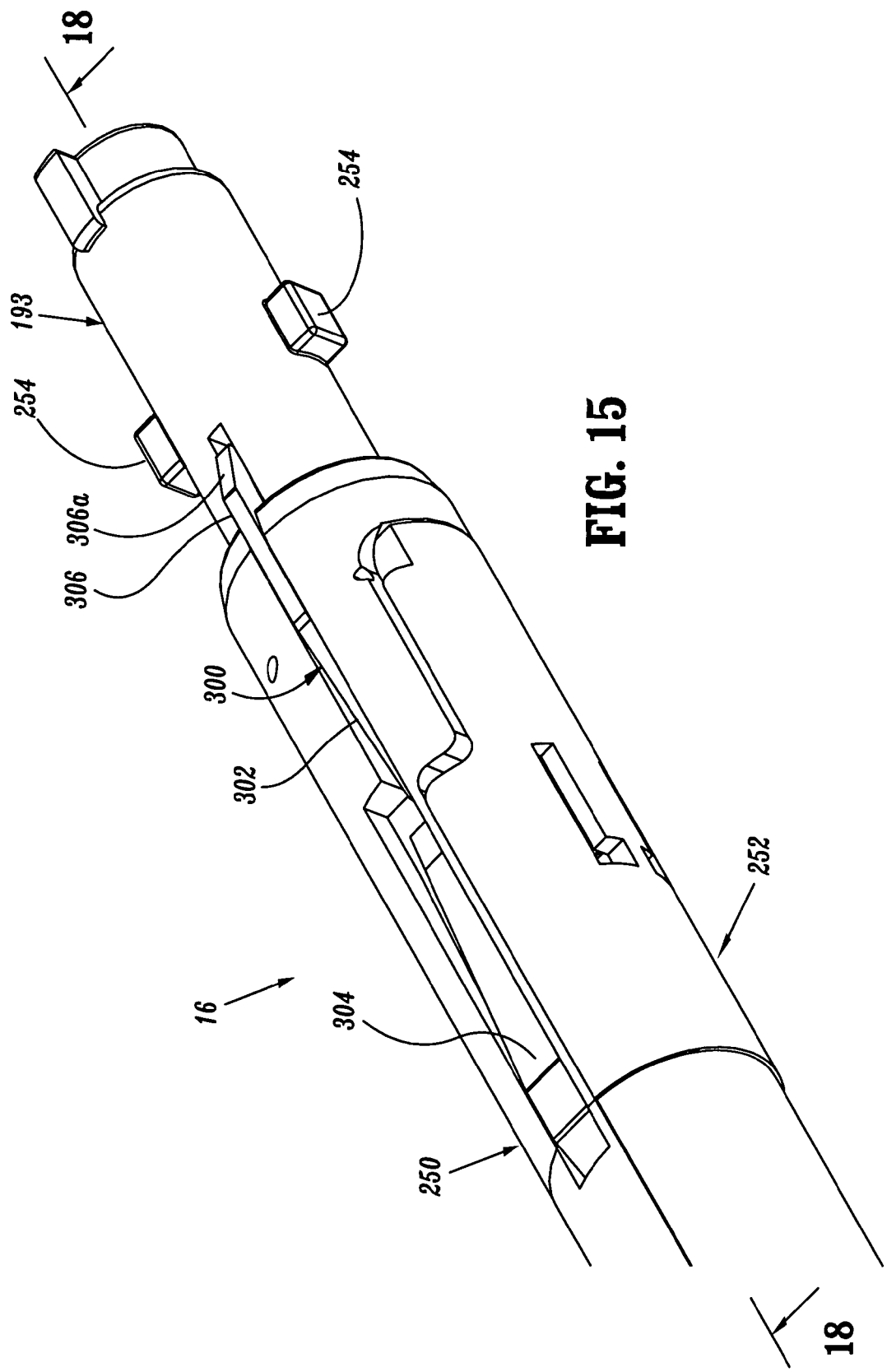
FIG. 15 is an enlarged perspective view of the proximal end of the DLU of FIGS. 6-9 illustrating a locking mechanism according to the present disclosure.
Figure 17:
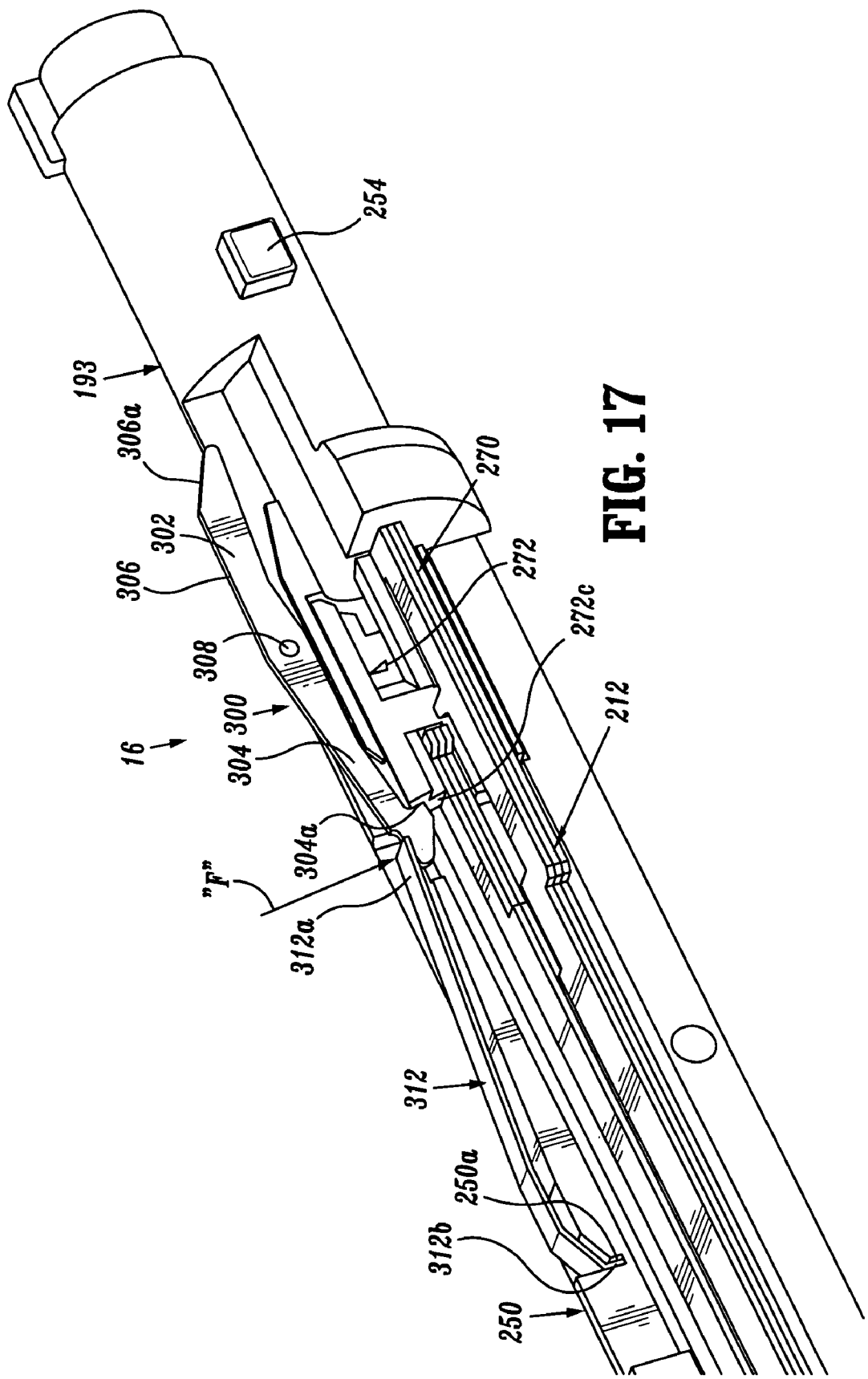
FIG. 17 is an enlarged perspective view, partially broken-away, of the proximal end of the DLU of FIG. 15 illustrating the locking mechanism in a first position.
Figure 18:
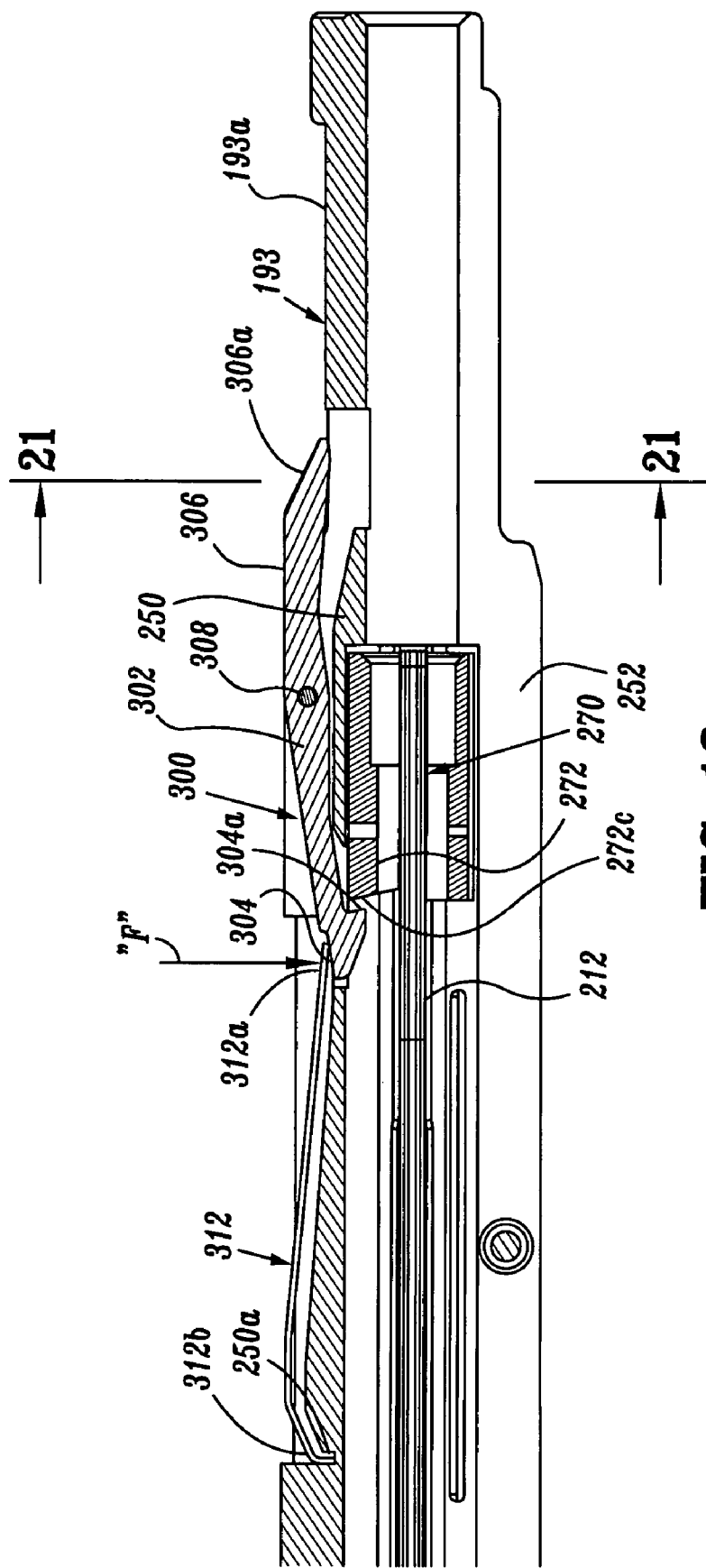
FIG. 18 is a longitudinal cross-sectional view of the proximal end of the DLU of FIGS. 6-9, as taken through 18-18 of FIG. 15, with the locking mechanism in a first position.

Prior to attachment of DLU 16 to surgical stapling apparatus 10, lever 302 of locking mechanism 300 is urged to the locked position by spring 312 (FIGS. 15, 17 and 18). As discussed above, in the locked position, lever 302 is pivoted about pivot pin 308 such that hook member 304a of lever 302 is in engagement with a distal face 272c, of drive member 272 and proximal end 306 is positioned radially outward of an outer surface 193a of insertion tip 193 (see FIG. 18). In this locked position, hook member 304a prevents inadvertent distal advancement of drive member 272 to maintain drive member 272 in its proximal-most ready-to-load position. This ensures that engagement section 270 of drive assembly 212 properly engages the distal end 276 of control rod 52 (see FIG. 14) of stapling apparatus 10 when DLU 16 is mounted to elongated body 14 of stapling apparatus 10. Distal end 276 of control rod 52 has one or more engagement surfaces, preferably, and here shown as, including a head 276a and a smaller diameter annular recess 276b just proximal of head 276a and partially defined by head 276a.

Figure 20:
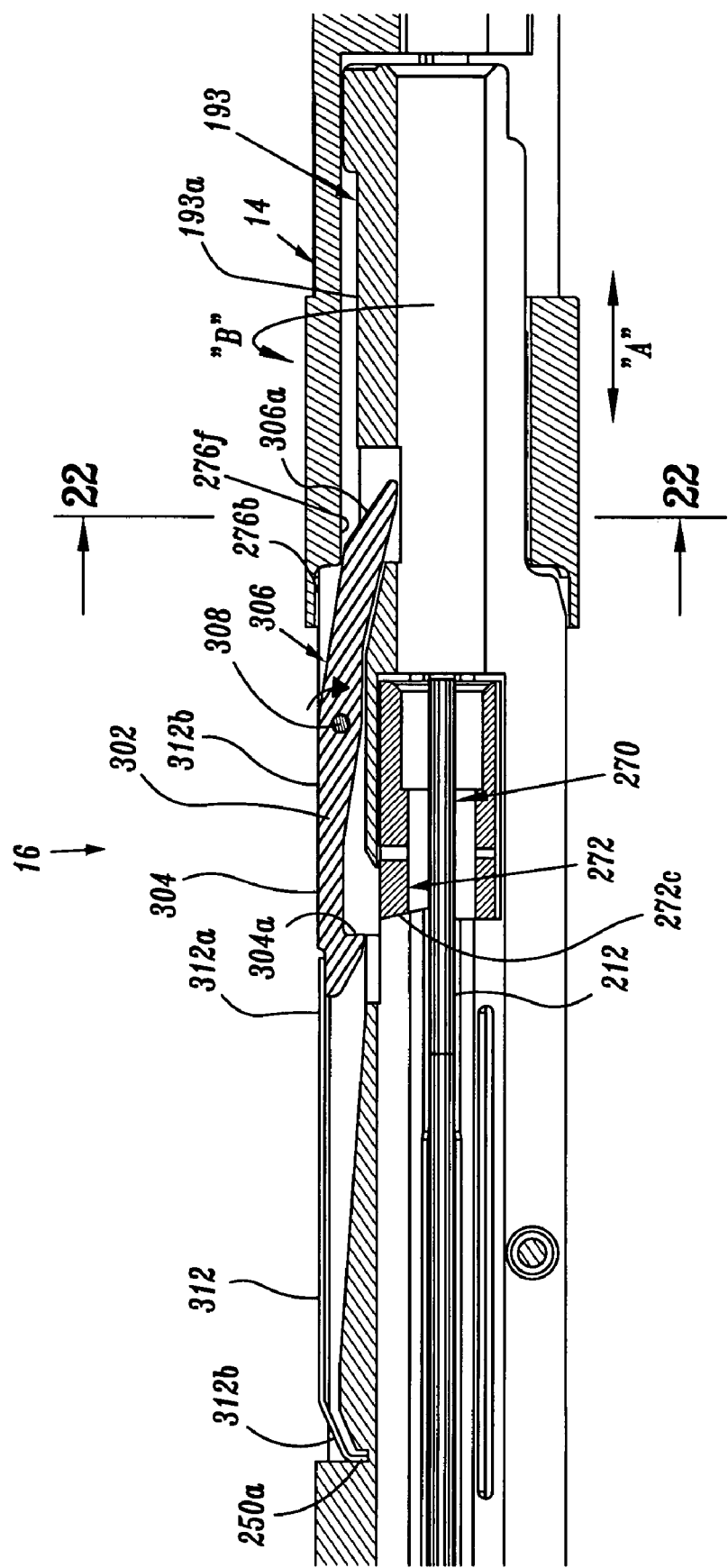
FIG. 20 is a longitudinal cross-sectional view of the proximal end of the DLU of FIGS. 6-9 as taken through 18-18 of FIG. 15, with the locking mechanism in a second position.
Figure 23:
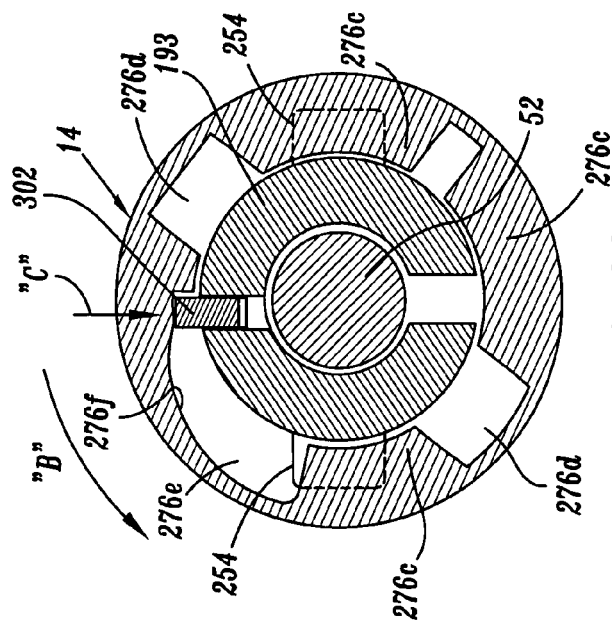
FIG. 23 is an enlarged transverse cross-sectional view of the proximal end of the DLU of FIGS. 6-9, as would be taken through 22-22 of FIG. 20, illustrating the position of the locking mechanism following rotation of the DLU relative to the elongate body.
Figure 22:
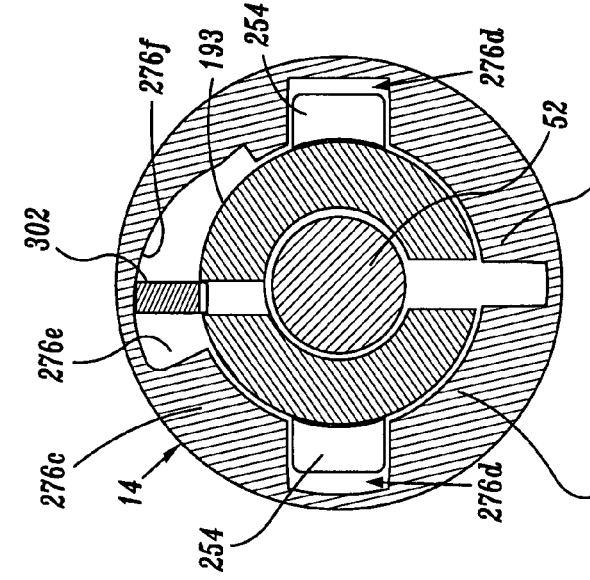
FIG. 22 is an enlarged transverse cross-sectional view of the proximal end of the DLU of FIGS. 6-9, as taken through 22-22 of FIG. 20, illustrating the position of the locking mechanism prior to the rotation of the DLU relative to the elongate body.
Figure 21:
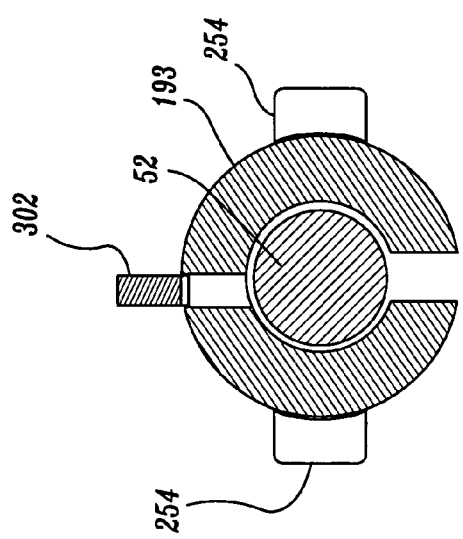
FIG. 21 is an enlarged transverse cross-sectional view of the proximal end of the DLU of FIGS. 6-9, as taken through 21-21 of FIG. 18.

When DLU 16 is mounted to elongated body 14 of stapling apparatus 10, in a manner to be discussed in further detail below, angled surface 306a of proximal end 306 of lever 302 engages sloping surface 276f of elongate body 14 (see FIGS. 20, 22 and 23). Engagement between angled surface 306a and sloping surface 276f pivots or rotates lever 302 about pivot pin 308 to cam proximal end 306 of lever 302 radially inwardly. Movement of proximal end 306 radially inwardly effects movement of hook 304a radially outwardly against force "F" of spring 312, such that hook 304a is released from and/or otherwise disengaged from drive member 272 to free drive assembly 212 and enable the operation or continued operation of surgical stapling apparatus 10.

Figure 16:
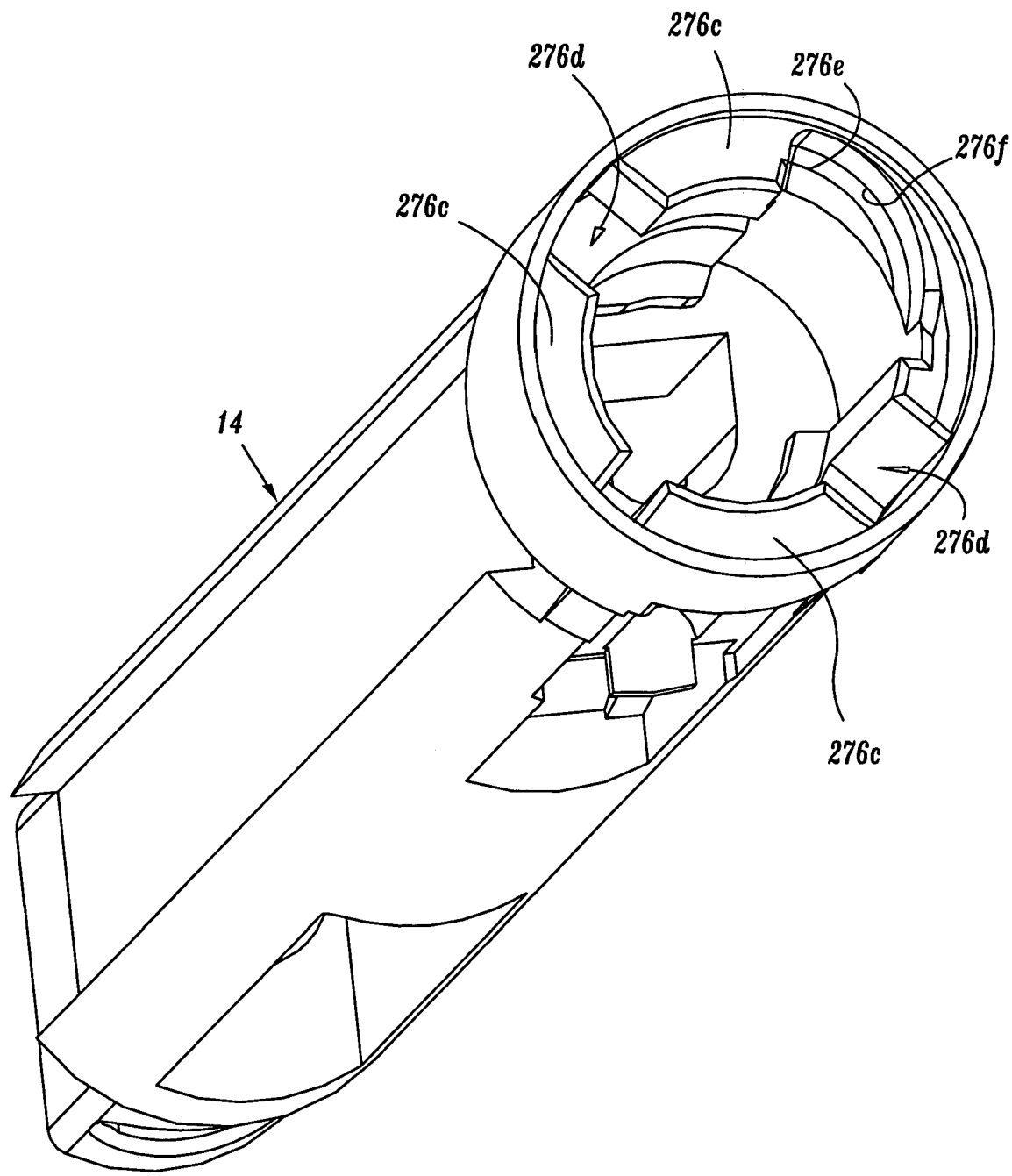
FIG. 16 is an enlarged perspective view of a distal end of the elongate body of the stapling apparatus in accordance with the present disclosure.

As best seen in FIG. 16, preferably the distal end of elongate body 14 includes a recess 276e formed therein having a shape to facilitate manipulation of locking mechanism 300 from the first position to the second position. Preferably, recess 276e includes a sloping surface 276f against which angled surface 306a of lever 302 contacts. In particular, sloping surface 276f is shaped such that twisting of DLU 16 in relation to elongated body 14 of stapling apparatus 10, after insertion tip 193 of DLU 16 has been inserted into the distal end of elongate body 14, results in proximal end 306 of lever 302 being progressively urged or cammed radially inward. Only after DLU 16 has been rotated over a sufficient arc in relation to body 14 will proximal end 306 of lever 302 be cammed radially inwardly a distance sufficient to release hook member 304a from drive member 272.

Figure 19:
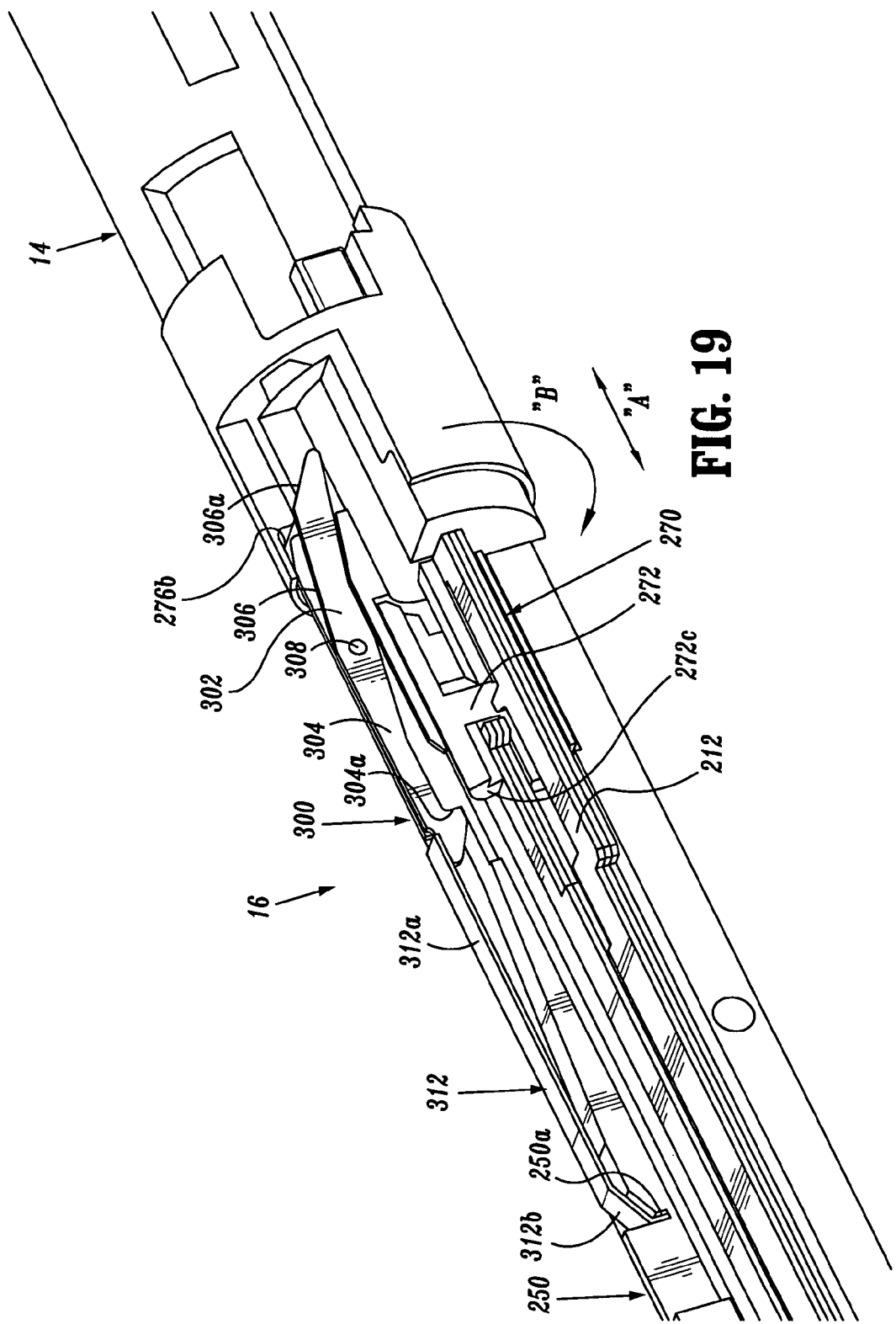
FIG. 19 is an enlarged perspective view, partially broken-away, of the proximal end of the DLU of FIG. 15 illustrating the locking mechanism in a second position.

With continued reference to FIGS. 15-23, a method of use and/or operation of locking mechanism 300, when securing DLU 16 to the distal end of elongate body 14, will be discussed. Initially, with locking mechanism 300 in the first position such that hook 304a is in engagement with drive member 272, insertion tip 193 of DLU 16 is introduced longitudinally into the distal end of elongate body 14, in either direction of arrow "A" (FIG. 19). As seen in FIGS. 19, 20 and 22, during introduction of insertion tip 193 into the distal end of elongate body 14, proximal end 306 of lever 302 enters recess 276b (FIG. 20) formed in the distal end of elongate body 14.

When insertion tip 193 has been fully inserted into the distal end of elongate body 14, and more particularly, when nubs 254 have completely entered channels 276d (FIGS. 16, 22 and 23), DLU 16 is rotated, in the direction of arrow "B" (FIGS. 19 and 23), such that sloping surface 276f of recess 276e acts against and engages angled surface 306a of proximal end 306 of lever 302. As described above, the camming action between sloping surface 276f of recess 276e and angled surface 306a of proximal end 306 causes proximal end 306 of lever 302 to be urged radially inward, as indicated by arrow "C" of FIG. 23, and about pivot pin 308, thereby overcoming force "F" of spring 312, and urging distal end 304 radially outward such that lever 302 is urged from the first position to the second position. Displacement of distal end 304 in a radially outward direction results in hook 304a becoming disengaged from drive member 272 thereby freeing drive assembly 212 for the continued operation of surgical stapling apparatus 10. DLU 16 is considered to be loaded to elongate body 14 when lever 302 is in the second position, e.g., when drive assembly 212 is connected to drive member or control rod 52 of elongate body 14.

Accordingly, the attachment of a DLU, having a drive assembly 212, to the distal end of elongate body 14 when drive assembly 212 is not in its proximal-most or proper loading position is prevented.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A surgical apparatus, comprising:
a handle assembly;
an elongate body extending from the handle assembly and defining a longitudinal axis, the elongate body having a drive member extending therethrough;
a tool assembly supported adjacent a distal end of the elongate body, the tool assembly including a staple cartridge having surgical staples;
a drive assembly arranged for longitudinal movement with the drive member and arranged for engagement with the tool assembly for applying the surgical staples; and
a locking mechanism having a pivoting member with a first end, a second end and an intermediate pivot point, the first end being movable from an initial position, in which the pivoting member is in engagement with a portion of the drive assembly to substantially prevent longitudinal movement thereof, to at least one subsequent position, in which the pivoting member is disengaged from the drive assembly to allow longitudinal movement thereof, the pivoting member being movable from the initial position to the at least one subsequent position in a radial direction relative to the longitudinal axis, the second end being radially movable in directions opposite to the first end to actuate the locking mechanism, wherein the elongate body has a surface for engaging the pivoting member when the loading unit is loaded to the elongate body.

2. The surgical apparatus according to claim 1, wherein the locking mechanism is positioned distally of the handle assembly.

3. The surgical apparatus according to claim 2, wherein the locking mechanism is positioned distally of the handle assembly when the surgical apparatus is in an assembled condition.

4. The surgical apparatus according to claim 1, wherein the first end of the pivoting member is moved radially inward relative to the longitudinal axis and the second end of the pivoting member is moved radially outward relative to the longitudinal axis in moving from the initial position to the at least one subsequent position.

5. The surgical apparatus according to claim 1, wherein the pivoting member is biased so that the second end is urged toward a radially inward direction relative to the longitudinal axis.

6. The surgical apparatus according to claim 1, further comprising a loading unit for loading to the elongate body, the loading unit including the tool assembly, the drive assembly being configured to removably engage the drive member when the loading unit is loaded to the elongate body.

7. The surgical apparatus according to claim 1, wherein the pivoting member is moved from the initial position to the at least one subsequent position when the loading unit is loaded to the elongate body.

8. The surgical apparatus according to claim 7, wherein the loading unit has a proximal body portion.

9. The surgical apparatus according to claim 8, wherein the proximal body portion has an insertion tip and the elongate body has a distal end for receiving the insertion tip.

10. A surgical apparatus, comprising:
a handle assembly;
an elongate body extending from the handle assembly and defining a longitudinal axis, the elongate body having a drive member extending therethrough;
a tool assembly supported adjacent a distal end of the elongate body, the tool assembly including a staple cartridge having surgical staples;
a drive assembly arranged for longitudinal movement with the drive member and arranged for engagement with the tool assembly for applying the surgical staples; and
a locking mechanism positioned externally of the handle assembly and having a pivoting member movable from an initial position, in which the pivoting member is in engagement with a portion of the drive assembly to substantially prevent longitudinal movement thereof, to at least one subsequent position, in which the pivoting member is disengaged from the drive assembly to allow longitudinal movement thereof, the pivoting member being movable from the initial position to the at least one subsequent position in a radial direction relative to the longitudinal axis, wherein the elongate body has a surface for engaging the pivoting member when the loading unit is loaded to the elongate body.

11. The surgical apparatus according to claim 10, wherein the pivoting member has a distal end, a proximal end, and a pivot point, the distal end and the proximal end being movable about the pivot point in radially opposite directions relative to the longitudinal axis.

12. The surgical apparatus according to claim 11, wherein the distal end of the pivoting member engages the portion of the drive assembly in the initial position.

13. The surgical apparatus according to claim 12, wherein the proximal end of the pivoting member is moved radially inward relative to the longitudinal axis and the distal end of the lever is moved radially outward relative to the longitudinal axis in moving from the initial position to the at least one subsequent position.

14. The surgical apparatus according to claim 12, wherein the pivoting member is biased so that the distal end is urged toward a radially inward direction relative to the longitudinal axis.

15. The surgical apparatus according to claim 10, further comprising a loading unit for loading to the elongate body, the loading unit including the tool assembly, the drive assembly being configured to removably engage the drive member when the loading unit is loaded to the elongate body.

16. The surgical apparatus according to claim 10, wherein the pivoting member is moved from the initial position to the at least one subsequent position when the loading unit is loaded to the elongate body.

17. The surgical apparatus according to claim 16, wherein the loading unit has a proximal body portion.

18. The surgical apparatus according to claim 17, wherein the proximal body portion has an insertion tip and the elongate body has a distal end for receiving the insertion tip.

* * * * *